United States Patent [19]

Krenitsky

[11] Patent Number: 4,544,634
[45] Date of Patent: Oct. 1, 1985

[54] METHOD OF PRODUCING ACYCLOVIR

[75] Inventor: Thomas A. Krenitsky, Chapel Hill, N.C.

[73] Assignee: Burroughs Wellcome Co., Research Triangle Park, N.C.

[21] Appl. No.: 434,384

[22] Filed: Oct. 14, 1982

[51] Int. Cl.$^4$ .................. C12P 17/18; A01N 43/90; A61K 31/52
[52] U.S. Cl. ........................ 435/119; 514/261; 514/934
[58] Field of Search ................. 435/119, 88

[56] References Cited

FOREIGN PATENT DOCUMENTS 0074306 3/1983 European Pat. Off. .
0085424 8/1983 European Pat. Off. .

OTHER PUBLICATIONS

Krenitsky et al., Archive of Biochemistry and Biophysics, vol. 185, No. 2, pp. 370–375, Jan. 30, 1978; vol. 150, No. 2, pp. 585–599, Jun. 1972.

Primary Examiner—Alvin E. Tanenholtz
Attorney, Agent, or Firm—Donald Brown

[57] ABSTRACT

The novel compound 6-deoxyacyclovir is enzymatically converted to acyclovir by xanthine oxidase/dehydrogenase or aldehyde oxidase in vivo, i.e. within the body of the animal being treated. The enzymatic conversion may also be effected ex vivo (i.e. in vitro) as a method of synthesizing acyclovir.

9 Claims, No Drawings

METHOD OF PRODUCING ACYCLOVIR

The present invention relates to antiviral purine derivatives containing an acyclic chain in the 9-position.

U.K. Patent Specification No. 1523865 and U.S. Pat. No. 4,199,574 describe a broad class of purine derivatives containing an acyclic side chain in the 9-position. These purine derivatives have been found to have antiviral activity against various classes of DNA viruses particularly against herpes viruses such as herpes simplex.

Among these derivatives, 9-(2-hydroxyethoxymethyl)guanine (otherwise known as acyclovir) has been found to have particularly good activity against herpes viruses such as herpes simplex. However, while acyclovir has been found to be especially effective upon topical or parenteral administration, it is only moderately well absorbed upon oral administration with corresponding levels of drug in the plasma. It will be appreciated that when one is treating an internal disorder by oral administration of a drug, it is clearly desirable that the drug should be well absorbed from the gastro-intestinal tract with resulting high plasma levels.

The surprising discovery has now been made that 6-deoxyacyclovir, a purine derivative, falling within the scope of the compounds broadly described in U.K. Patent Specification No. 1523865 and characterized by the presence of a hydrogen atom in the 6-position of the purine nucleus, can be readily converted in vivo by the action of the molybdo-flavo-protein enzymes xanthine oxidase/dehydrogenase or aldehyde oxidase into the corresponding 6-hydroxy purine derivative acyclovir. Furthermore, from experiments in rats, it has been found that oral administration of 6-deoxyacyclovir results in efficient absorption from the gastro-intestinal tract and high plasma levels of the corresponding acyclovir, formed by enzymatic conversion of the 6-hydrogen compound. Indeed, it has been found that with oral administration higher blood levels of acyclovir are obtainable with 6-deoxyacyclovir than with acyclovir itself.

Also, for example, 6-deoxyacyclovir, i.e. 2-amino-9-(2-hydroxyethoxymethyl)purine, the 6-hydrogen analogue of acyclovir, is considerably more soluble in water than acyclovir, the former compound having a solubility of 50 mg/ml and the latter having a solubility of 1.25 mg/ml at 25° C. This improved water-solubility enables 6-deoxyacyclovir to be used in a greater variety of aqueous pharmaceutical formulations which require some solubilisation of the drug. The above-mentioned 6-hydrogen purine analogue 6-deoxyacyclovir may be represented by the formula (I)

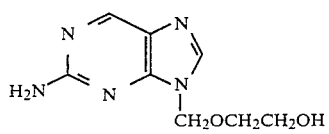

(I)

and physiologically acceptable salts thereof.

Salts of the compounds of formula (I) which may be conveniently used in therapy include physiologically acceptable salts of organic acids such as lactic, acetic, malic or p-toluenesulphonic acid as well as physiologically acceptable salts of mineral acids such as hydrochloric or sulphuric acid.

It is thus possible to synthesize acyclovir in the body (i.e. in vivo) by administering 6-deoxyacyclovir to mammals including humans wherein the 6-deoxyacyclovir is acted upon by xanthine oxidase/dehydrogenase or aldehyde oxidase in the body and is thereby converted into acyclovir. It has also been demonstrated that acyclovir may be synthesized, i.e. manufactured, by the ex vivo (i.e. in vitro) enzymatic oxidation of 6-deoxyacyclovir by the actions of the molybdo-flavo-protein enzymes xanthine oxidase/dehydrogenase or aldehyde oxidase. Oxygen or other appropriate electron acceptors such as ferricyanide ion or methylene blue may serve as the oxidizing agent. Microorganisms which contain or produce xanthine oxidase/dehydrogenase may be used to effect the conversion of 6-deoxyacyclovir to acyclovir.

The discovery that the 6-hydrogen purine of formula (I) above can be readily converted into its corresponding 6-hydroxy analogue is surprising since in previous studies with xanthine oxidase from bovine milk (H. Lettre et al. (1967) Biochem. Pharmacol., 16, 1747–1755; T. A. Krenitsky et al. (1972) Arch. Biophys., 150, 585–599) it was shown that 9-substitution obliterates or greatly diminishes the rate at which a variety of purines are oxidized. In view of these observations, it was surprising to find that this enzyme oxidized for example 6-deoxyacyclovir, a 9-substituted derivative of 2-aminopurine, at a faster rate than the 9-unsubstituted purine, as established from enzyme studies.

The high level of absorption of the compound of formula (I) from the gastrointestinal tract renders the compound especially useful when oral administration of the compound is desired, e.g. in the treatment of diseases caused by various DNA viruses, such as herpes infections for example herpes simplex, varicella or zoster or Epstein-Barr virus. In addition to its use in human medical therapy the compound of formula (I) can be administered to other animals for the treatment or prophylaxis of viral diseases, e.g. in other mammals.

According to a further feature of the present invention there is provided the compound of formula (I) and physiologically acceptable salts thereof for use in the treatment or prophylaxis of a viral disease in an animal, e.g. a mammal such as man.

The present invention also provides a method for the treatment or prophylaxis of a viral disease in an animal, e.g. a mammal such as man which comprises administering to the animal an effective antiviral amount of a compound of formula (I) or a physiologically acceptable salt thereof.

The compound of formula (I) and the physiologically acceptable salts thereof (hereafter collectively referred to as the active ingredients) may be administered by any route appropriate to the condition to be treated, suitable routes including oral, rectal, nasal, topical (including buccal and sublingual), vaginal and parenteral (including subcutaneous, intramuscular, intravenous, intradermal, intrathecal and epidural). It will be appreciated that the preferred route may vary with for example the condition of the recipient.

For each of the above-indicated utilities and indications the amount required of an active ingredient (as above defined) will depend upon a number of factors including the severity of the condition to be treated and the identity of the recipient and will ultimately be at the discretion of the attendant physician or veterinarian. In general however, for each of these utilities and indications, a suitable, effective dose will be in the range 0.1 to 250 mg per kilogram body weight of recipient per day, preferably in the range 1 to 100 mg per kilogram body weight per day and most preferably in the range 5 to 20 mg per kilogram body weight per day; an optimum dose is about 10 mg per kilogram body weight per day. (Unless otherwise indicated all weights of active ingredient are calculated as the parent compound of formula (I): for salts thereof the figures would be increased proportionately.) The desired dose is preferably presented as two, three, four or more sub-doses administered at appropriate intervals throughout the day. These sub-doses may be administered in unit dosage forms, for example, containing 10 to 1000 mg, preferably 20 to 500 mg and most preferably 100 to 400 mg of active ingredient per unit dosage form.

While it is possible for the active ingredients to be administered alone it is preferable to present them as pharmaceutical formulations. The formulations, both for veterinary and for human use, of the present invention comprise at least one active ingredient, as above defined, together with one or more acceptable carriers therefor and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

For infections of the eye or other external tissues e.g. mouth and skin, the formulations are preferably applied as a topical ointment or cream containing the active ingredient in an amount of, for example, 0.075 to 20% w/w, preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active ingredient through the skin or other affected areas. Examples of such dermal penetration enhancers include dimethylsulphoxide and related analogues.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl mono-stearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient.

Formulations suitable for vaginal administration may be presented as pessaries, tampons, creams, gels, pastes, foams or sray formulations containing in addition to the active ingredient such carriers as are known in the art to be appropriate.

Formulations suitable for parenteral administration include aqueous and non-aqueous sterile injection solution which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

The present invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

For oral administration the compositions can be in the form of a tablet, granule, drench, paste, cachet, capsule or feed supplement. Granules may be made by the well known techniques of wet granulation, precompression or slugging. They can be administered to animals in an inert liquid vehicle so as to form a drench, or in a suspension with water or oil base. Preferably further accessory ingredients such as a dispensing agent are included. These formulations preferably contain from 15 to 85% of the active ingredient.

A paste may be formulated by suspending the active ingredient in a liquid diluent. A stiffening or thickening agent may be included together with a wetting agent or a humectant if the liquid is water. If an emulsion paste is needed then one or more surface active agents should desirably be included. From 25 to 80% weight of these paste formulations may comprise the active ingredient.

In feed supplements the active ingredient is generally present in large amounts relative to the accessory ingredients, and the supplements may be added directly or after intermediate blending or dilution. Examples of accessory ingredients for such formulations include solid, orally ingestible carriers such as corn meal, soya flour, wheat shorts, soya grits, edible vegetable materials and fermentation residues. The active ingredient is usually incorporated in one or more of the accessory ingredients and intimately and uniformly dispersed by grinding, tumbling or stirring with conventional apparatus. Formulations containing 1 to 90% by weight of the active ingredient are suitable for adding to feeds.

For the treatment of herpes infections in horses, an oral or parenteral dose of from 0.1 to 250 mg per kg body weight per day, preferably from 2 to 100 mg per kg per day may be required. The dose may be split up into discrete units administered at regular intervals during the day, and repeated daily for up to 14 days or until the infection is cleared. For viral infections in other animals the dose may vary depending on the size and metabolism of the animal. The compositions may be administered in unit dosage form, such as a tablet a few times daily in the amount of 10 to 1000 mg per unit dose.

The compound of formula (I) and physiologically acceptable salts thereof may be prepared in conventional manner by analogous processes for preparing compounds of similar structure, such as those methods described in U.K. Patent Sepcification No. 1523865.

The following Examples illustrate the present invention.

EXAMPLE 1

2-Amino-9-(2-hydroxyethoxymethyl)purine

A mixture of 2.48 g (7.13 mM) of 2-amino-6-chloro-9-(2-benzoyloxyethoxymethyl)purine, 250 ml of absolute ethanol, 1.9 ml of triethylamine and 0.6 g of 5 palladium on charcoal was shaken under hydrogen at an initial pressure of 50 p.s.i. at room temperature for twenty hours. The mixture was filtered, 0.265 g of fresh palladium catalyst and 1.9 ml of triethylamine were added and the mixture shaken under hydrogen for an additional 16 hours.

The ethanolic solution, after filtration through a pad of Celite was evaporated in vacuo, and the resulting white solid extracted with boiling benzene several times. The benzene extracts were concentrated, combined with 20 ml of 40% aqueous methylamine and 20 ml of methanol and allowed to evaporate in an open flask on a steam bath to dryness. The resulting mixture was triturated with ether to remove the N-methylbenzamide and then recrystallized from 100% ethanol to yield 2-amino-9-(2-hydroxyethoxymethyl)purine as analytically pure white granules, m.p.=186°–187.5° C.

EXAMPLE 2

Enzymatic Synthesis of Acyclovir

A solution (20 $\mu$L) of a purified bovine milk xanthine oxidase containing 1.06 units (nmoles of xanthine oxidized per minute) of activity was added to 500 $\mu$L of a solution 43.6 $\mu$M with respect to 6-deoxyacyclovir, 0.05M with respect to potassium phosphate and 0.13 mM with respect to ethylenediaminetetraacetic acid at pH 6.8 and 25° C. The reaction mixture was equilibrated with atmospheric oxygen, and the oxygen served as the electron acceptor. UV monitoring indicated nearly complete conversion to acyclovir after 24 hours. The identity of acyclovir as the product of the reaction was confirmed by its NMR spectrum.

The following Examples 3 to 7 illustrate pharmaceutical formulations according to the invention where the active compound is a compound of formula (I) or a physiologically acceptable salt thereof.

| Tablet Example 3 | |
|---|---|
| Active compound | 100 mg |
| Lactose | 200 mg |
| Starch | 50 mg |
| Polyvinylpyrrolidone | 5 mg |
| Magnesium stearate | 4 mg |
| | 359 mg |

Tablets were prepated from the foregoing ingredients by wet granulation followed by compression.

| Injectable Solution Example 4 | |
|---|---|
| Active compound | 0.775 g |
| Sterile, pyrogen-free, pH 7 phosphate buffer to | 25 ml |

| Ophthalmic Solution Example 5 | |
|---|---|
| Active compound | 1.0 g |
| Sodium chloride, analytical grade | 0.9 g |
| Thiomersal | 0.001 g |
| Purified water to | 100 ml |
| pH adjusted to | 5.5–7.5 |

| Oil based Paste Example 6 | |
|---|---|
| China Clay (solid diluent) | 20.0% w/w |
| Mineral Oil* (liquid diluent) | 60.0% w/w |
| Active compound | 20.0% w/w |

The components were mixed to provide a paste of uniform consistency.

| Feed Supplement - Pellets Example 7 | |
|---|---|
| Active compound | 1% |
| Cereal Base | 99% |

The two ingredients were mixed then fed to any conventional feed stuff pelleting plant.

Biological Activity

The following experiments were carried out to determine the urinary excretion and plasma levels of acyclovir after oral dosing of rats with acyclovir, 6-deoxyacyclovir and the 6-amino analogue thereof i.e. 2,6-diamino-9-(2-hydroxyethoxymethyl)purine, hereinafter referred to as aminoacyclovir. The latter compound is a prodrug of acyclovir (Good S. S. and de Miranda P., Fed. Proc. (1982), 41, 1733) which depends on adenosine deaminase for conversion to acyclovir in vivo.

Procedure

Long Evans male rats were dosed by intragastric needle with the drug and placed in metabolic cages which separated urine from feces. The collected urine and plasma samples were analyzed for acyclovir content by a radioimmunoassay (Quinn, R. P., et al., Anal. Biochem., 98, 319 (1979)). It was demonstrated that neither aminoacyclovir nor 6-deoxyacyclovir cross reacted with the antisera used in the assay.

Results

The results are given below in Tables I and II

TABLE I

The urinary excretion of acyclovir after oral dosing of rats with acyclovir, aminoacyclovir and 6-deoxyacyclovir

| Dose mg/kg | Urine Samples | Acyclovir | % Dose Excreted as Acyclovir (No. of Animals) | |
|---|---|---|---|---|
| | | | Aminoacyclovir | 6-Deoxyacyclovir |
| 5 | 0–24 hr | — | 24.7 (2) | 67.0 (1) |
| | 24–48 hr | — | 0.4 (2) | 0.2 (1) |
| 20 | 0–24 hr | — | 24.8 (2) | 69.1 (1) |
| | 24–48 hr | — | 0.3 (2) | 0.3 (1) |
| 25 | 0–48 hr | 19.2 (4) | — | — |

TABLE II

A comparison of the plasma levels of acyclovir achieved after oral dosing of rats with deoxyacyclovir and with aminoacyclovir

| Hr after a 20 mg/kg dose | μM Acyclovir Concentrations in Plasma | | |
|---|---|---|---|
| | Aminoacyclovir Rat 1 | 6-Deoxyacyclovir Rat 2 | Rat 3 |
| 0.5 | 2.75 | | 30 |
| 1 | 3.03 | 16.6 | 18.6 |
| 2 | 2.48 | 4.96 | 17.5 |
| 4 | 0.93 | 1.00 | 6.7 |
| 6 | 0.34 | 0.41 | 4.06 |
| 20 | <0.1 | <0.1 | 0.25 |

Toxicity Study

Two male and 2 female Beagle dogs were given 6-deoxyacyclovir per os (once daily for 5 consecutive days) at a dose level of 40 mg/kg/day. There were no effects in 1 male and 1 female sacrificed at the end of the treatment period or in 1 male and 1 female sacrificed after a 2 week post-dose period.

I claim:

1. A method of producing acyclovir which comprises converting 6-deoxyacyclovir or a physiologically acceptable salt thereof in an aqueous liquid in the presence of oxygen and xanthine oxidase to produce said acyclovir.

2. The method of claim 1 in which the salt is an acid addition salt.

3. The method of claim 1 in which the salt is the salt of lactic, acetic, malic, p-toluenesulphonic, hydrochloric or sulphuric acid.

4. A method of producing acyclovir which comprises converting 6-deoxyacyclovir or a physiologically acceptable salt thereof in an aqueous liquid in the presence of oxygen and aldehyde oxidase to produce said acyclovir.

5. The method of claim 4 in which the salt is an acid addition salt.

6. The method of claim 5 in which the salt is the salt of lactic, acetic, malic, p-toluenesulphonic, hydrochloric or sulphuric acid.

7. A method of producing acyclovir which comprises converting 6-deoxyacyclovir or a physiologically acceptable salt thereof in an aqueous liquid in the presence of oxygen and xanthine dehydrogenase to produce said acyclovir.

8. The method of claim 7 in which the salt is an acid addition salt.

9. The method of claim 8 in which the salt is the salt of lactic, acetic, malic, p-toluenesulphonic, hydrochloric or sulphuric acid.

* * * * *